(12) United States Patent
Li et al.

(10) Patent No.: US 11,333,647 B2
(45) Date of Patent: May 17, 2022

(54) APPARATUS FOR ASSESSING HOT COAL FALLOUT PROPENSITY OF BURNING CIGARETTE BASED ON HUMAN BEHAVIOR FEATURES OF ASH-FLICKING ACTION AND METHOD THEREOF

(71) Applicants: ZHENGZHOU TOBACCO RESEARCH INSTITUTE OF CNTC, Zhengzhou (CN); HEFEI INSTITUTE OF PHYSICAL SCIENCE, CHINESE ACADEMY OF SCIENCES, Hefei (CN); CHINA TOBACCO JIANGXI INDUSTRIAL CO., LTD., Nanchang (CN)

(72) Inventors: Bin Li, Zhengzhou (CN); Yi Zhang, Nanchang (CN); Yaoshuo Sang, Hefei (CN); Mingjian Zhang, Zhengzhou (CN); Liu Hong, Nanchang (CN); Zhigang Li, Hefei (CN); Bingyang Xu, Nanchang (CN); Zhenyu Xu, Nanchang (CN); Xiaoling Tang, Nanchang (CN); Long Zhang, Hefei (CN)

(73) Assignees: ZHENGZHOU TOBACCO RESEARCH INSTITUTE OF CNTC, Zhengzhou (CN); HEFEI INSTITUTE OF PHYSICAL SCIENCE, CHINESE ACADEMY OF SCIENCES, Hefei (CN); CHINA TOBACCO JIANGXI INDUSTRIAL CO., LTD., Nanchang (CN)

(*) Notice: Subject to any disclaimer, the term of this patent is extended or adjusted under 35 U.S.C. 154(b) by 267 days.

(21) Appl. No.: 16/608,150

(22) PCT Filed: Apr. 28, 2018

(86) PCT No.: PCT/CN2018/085078
§ 371 (c)(1),
(2) Date: Nov. 4, 2019

(87) PCT Pub. No.: WO2018/202005
PCT Pub. Date: Nov. 8, 2018

(65) Prior Publication Data
US 2020/0150102 A1 May 14, 2020

(30) Foreign Application Priority Data
May 3, 2017 (CN) .......................... 201710303000.2

(51) Int. Cl.
*G01N 33/00* (2006.01)
*G01N 3/34* (2006.01)
(52) U.S. Cl.
CPC ............... *G01N 33/00* (2013.01); *G01N 3/34* (2013.01); *G01N 2203/0266* (2013.01)
(58) Field of Classification Search
CPC .. G01N 33/00; G01N 3/34; G01N 2203/0266; A24C 5/343
(Continued)

(56) References Cited

U.S. PATENT DOCUMENTS

2020/0146337 A1* 5/2020 Li .......................... A24C 5/343
2020/0333366 A1* 10/2020 Li .......................... G01N 1/2205

FOREIGN PATENT DOCUMENTS

CN     102937639    * 2/2013
CN     105651626    * 6/2016

\* cited by examiner

*Primary Examiner* — Octavia Hollington
(74) *Attorney, Agent, or Firm* — Lewis Roca Rothgerber Christie LLP

(57) ABSTRACT

The present disclosure provides a method for assessing hot coal fallout propensity of burning cigarettes based on human behavior features of ash-flicking action. The method is characterized in that the method is accomplished through an (Continued)

apparatus for detecting hot coal fallout propensity based on human behavior features of ash-flicking action, which include behavior features of human action of flicking cigarette ash, features of holding a cigarette, and features of force applying process and other aspects. This method can provide objective and accurate test basis for evaluation of cigarette fallout performance.

16 Claims, 2 Drawing Sheets

(58) Field of Classification Search
USPC .......................................................... 73/865.6
See application file for complete search history.

APPARATUS FOR ASSESSING HOT COAL FALLOUT PROPENSITY OF BURNING CIGARETTE BASED ON HUMAN BEHAVIOR FEATURES OF ASH-FLICKING ACTION AND METHOD THEREOF

CROSS-REFERENCE TO RELATED APPLICATION(S)

This application is a National Phase Patent Application of International Patent Application Number PCT/CN2018/085078, filed on Apr. 28, 2018, which claims priority of Chinese Patent Application 201710303000.2, filed May 3, 2017. The entire contents of both of which are incorporated herein by reference.

FIELD

The present disclosure belongs to the technical field of quality detection of cigarette products, and particularly relates to an apparatus for assessing hot coal fallout propensity of burning cigarettes based on human behavior features of ash-flicking action and a method thereof.

BACKGROUND

In recent years, consumers' resentment market feedback caused by hot coal fallout of burning cigarettes has occurred frequently, and the range of involved brands has become more extensive, especially in high-grade cigarette products. During the process of cigarette consumption, the combustion coal fallout of burning cigarettes may not only cause cigarette loss to interrupt smoking, but falling butts may also lead to clothing, furniture burning and risk of fire (Peace. World No Tobacco Day: Interpretation of fire accidents caused by cigarette butt [J]. China Fire, 2011 (11): 38-42.). The issue of cigarette fallout has been paid more attention, and the improvement approaches were hoped to be sought through technological innovation (WANG Haibin, LIU Dehu, WU Zhaogang, et al. Analysis and research on falling phenomenon of cigarette burning end [A]. China Tobacco Society 2010 Symposium Set, 2010, 285-287.).

Hot coal fallout of burning cigarettes may be caused by matching of burning rate of cigarette paper with tobacco, filling of tobacco in cigarette paper, control of axial distribution by an ecreteur of cigarette maker during cigarette production and so on. Assessment of fallout performance is an important basis for evaluating effectiveness of various technical improvements. Now, detection of fallout performance of burning cigarettes can only rely on consumer's conscious and qualitative judgment during cigarette smoking and flicking ash, leading to low efficiency and poor repeatability.

Chinese patent application (CN 102937639 A) has developed a fallout detection device for burning cigarettes by simulating consumer's action habits of flicking cigarette ash. This detection device determines the combustion coal fallout of burning cigarettes through intermittent tapping. The device uses a tapping method which is different from actual consumer's habit of flicking action, and test results of the method are too simple to give effective and objective evaluation.

A fallout detecting device for burning cigarettes involved in Chinese utility model application (CN 204165850 U) has improved problems in that the device disclosed in Chinese patent application (CN 102937639 A) cannot flexibly change tapping force and angle, but there are still some issues. The tapping method disclosed in the patent still relies on external mechanical force to strike cigarettes. Such tapping simulation may be performed by mechanical components with simple tapping action through surface tapping action, but actual stress situation in the process may be not considered in nature.

Chinese patent application (201310227468.X) has disclosed a device for detecting fallout propensity of burning cigarettes by rotation. The device is characterized in that it may comprise a base, a motor, a cigarette holding mechanism driven by the motor, and a safety shield. This disclosure tests hot coal fallout phenomenon of burning cigarettes by rotation, which has developed a new method for detecting hot coal. This new method obtains statistical data of fallout by multiple detections, thereby obtaining performance index of fallout propensity of burning cigarettes. The present disclosure has advantages in that rotation time and number of revolutions are controllable, different detection strengths can be applied on different samples, and a wide range of application can be obtained; the detection method is simple and convenient, spends short time, and has low detection cost. However, since there is no actual smoking process in this method, it does not meet human behavior of tapping ashes and flicking ashes, and there is still a problem in evaluating fallout performance of burning cigarettes in actual situation.

Chinese patent application (201510973214.1) provides an automatic control detection device and method for hot coal fallout performance of burning cigarettes. The device and method are designed by studying comparison of mechanical behavior between machine flicking ash and human flicking ash so as to ensure mechanical dynamics behavior caused by flicking ash through a mechanical device to be consistent with human dynamics behavior. This may provide a unified, objective and accurate detection method for fallout propensity detection of cigarettes. But this method has not yet described how to establish a cigarette fallout propensity detection method based on behavior features of consumer's action of flicking cigarette ash. However, such falling behavior features are basic issue of the proposed and applied method for cigarette fallout performance evaluation, and it is more important to establish a simulated detecting method based on behavior features of human action of flicking cigarette ash.

SUMMARY

An object of the present disclosure is provided based on the deficiencies and issues in the above patents. Data of falling behavior features of flicking cigarette ash of cigarette consumers is obtained by investigation of falling behavior features of flicking cigarette ash of the cigarette consumers. The present disclosure provides an apparatus for assessing hot coal fallout propensity of burning cigarettes based on human behavior features of ash-flicking action and a method thereof. The present disclosure provides objective and accurate detection basis for evaluation of fallout performance of burning cigarettes.

One aspect of the present disclosure may provide an apparatus for assessing hot coal fallout propensity of burning cigarettes based on human behavior features of ash-flicking action. The apparatus may comprise:

a holding unit for holding a cigarette;
a suction unit connected to one end of the cigarette to suck the cigarette;
a flicking unit disposed adjacent to the holding unit, and the flicking unit being capable of flicking the cigarette; and a control unit coupled with the suction unit and the flicking unit, respectively, to control suction and flicking actions.

In an embodiment, the holding unit may be held at a filter tip of the cigarette, and the one end is a free end of the filter tip.

In an embodiment, the flicking unit may comprise:
a flicking arm; and
a flicking hammer disposed at one end of the flicking arm to flick the cigarette under driving of the flicking arm, and an angle between the flicking arm and the cigarette being between 30°-60° when the flicking hammer is in contact with the cigarette.

In an embodiment, the flicking hammer may be made of a material with a Mohs hardness in a range of 1-3.

In an embodiment, a flicking strength of the flicking hammer applied on the cigarette is between 20 gf-60 gf.

In an embodiment, duration for every flicking action applied by the flicking hammer may be between 0.025 seconds-0.035 seconds.

In an embodiment, a width of a flicking point, where the flicking hammer flicks at the cigarette, may be between 9.5 mm-10.5 mm, and a distance between the flicking point and the one end may be between 30 mm-32 mm.

In an embodiment, the holding unit may be made of a material with a Shore hardness in a range of 0.4 HA-5.0 HA.

In an embodiment, a holding width of the holding unit holding the cigarette may be between 9.5 mm-10.5 mm, a holding strength of the holding unit may be between 16 gf-18 gf, and a distance from a holding point of the holding unit to the one end may be between 18 mm-20 mm.

In an embodiment, the control unit may be used to control a holding strength of the holding unit, a suction strength and a suction frequency of the suction unit, and a flicking cycle, a position of a flicking point and a flicking strength of the flicking unit.

Another aspect of the present disclosure may provide a method for assessing hot coal fallout propensity of burning cigarettes by using the apparatus for assessing hot coal fallout propensity of burning cigarettes. The method may comprise:

step A: using the holding unit to hold the cigarette and ignite the cigarette;

step B: activating the suction unit by the control unit to suck the cigarette, so as to simulate smoking action of human;

step C: taking k times suction by the suction unit as a cycle, and activating the flicking unit i by the control unit to perform a round of flicking actions on the cigarette to simulate human's flicking actions;

step D: stopping detection by the control unit when the cigarette has fallout or the cigarette is burned to a predetermined test termination mark; and step E: repeating the step B, the step C and the step D for 40 cigarettes, and recording an occurrence number n of fallout so as to calculate hot coal fallout propensity (HCFP) of burning cigarettes by using the following formula:

$$HCFP = n/40 \times 100\%.$$

In an embodiment, the step A, the step B, the step C, the step D, and the step E may be performed in a constant temperature and humidity environment.

In an embodiment, a holding width of the holding unit holding the cigarette may be between 9.5 mm-10.5 mm, and a holding strength of the holding unit may be between 16 gf-18 gf, and a distance from a holding point of the holding unit to the one end may be between 18 mm-20 mm.

In an embodiment, in the step C, the one round of flicking actions may comprise performing 1-4 times of flicking actions on the cigarette by using the flicking unit, and an interval time between adjacent two flicking actions is no longer than 1 second.

In an embodiment, the flicking unit may comprise a flicking arm and a flicking hammer, an angle between the flicking arm and the cigarette may be between 30-60 degrees when the flicking hammer is in contact with the cigarette.

In an embodiment, in the step C, a flicking strength of the flicking hammer applied on the cigarette may be between 20 gf-60 gf.

In an embodiment, in the step C, a width of a flicking point, where the flicking hammer flicks at the cigarette, may be between 9.5 mm-10.5 mm, and a distance between the flicking point and the one end may be between 30 mm-32 mm.

In an embodiment, two sets of tests may be applied to each cigarette sample, a final HCFP of the cigarette is represented by an average value of the two sets of detection results after the step E, and the detection may be performed again when an absolute difference of two sets of detection results is greater than 20%.

The presenting disclosure may investigate the behavior of flicking cigarette ash by consumers. As for King Size cigarettes and Superslim cigarettes sold in the market, the present disclosure may be embodied based on behavior of flicking cigarette ash to apply a force to the ash, and obtain behavior characteristics data when a smoker flicks the cigarette to cause cigarette ash fallen down according to falling features of action of flicking cigarette ash, features of holding a cigarette, and features of force applying process and other aspects. Test operating conditions in the method for detecting cigarette fallout propensity may be formed based on the above data. Therefore, objective and accurate test basis for evaluation of cigarette fallout performance may be provided, and technical data support may be provided to related cigarette fallout research.

Wherein: 1. Cigarette; 2. Flicking Angle (an angle formed by the center line of the flicking arm and the symmetry plane of the cigarette in the top view when a flicking arm moves to be parallel to a horizontal plane); 3. Flicking Arm; 4. Flicking Hammer; 5. Cigarette Holder; 6. Suction unit; X1. Holding Position; X2. Flicking Position; X3. Holder Width; X4. Hammer Width.

DETAILED DESCRIPTION

Specific embodiments of the present disclosure will be further described in detail with reference to the accompanying drawings.

The present disclosure investigates behavior of flicking cigarette ash by consumers. As for King Size cigarettes and Superslim cigarettes sold in the market, the present disclosure may be embodied based on behavior of flicking cigarette ash to apply a force to the ash, and obtain behavior characteristics data when a smoker flicks the cigarette to cause cigarette ash fallen down according to action features of flicking cigarette ash, features of holding a cigarette, and features of force applying process and other aspects. Operating conditions in the method for detecting cigarette fallout propensity may be formed based on the above data (as shown in Table 1).

TABLE 1 testing conditions for King Size cigarettes and Superslim cigarettes determined under ash-flicking action behavior.

| Force applying mode | Ash-flicking action behavior | |
|---|---|---|
| Cigarette Type | King Size | Superslim |
| Force Strength (gf) | 20 gf-60 gf | 20 gf-60 gf |
| Force Applying Time (s) | 0.03 ± 0.005 | 0.03 ± 0.005 |
| Force Applying Position (mm) | 30 ± 0.5 | 32 ± 0.5 |
| Holding Strength (gf) | 18 ± 2 | 16 ± 2 |
| Holding Position (mm) | 18 ± 0.5 | 19 ± 0.5 |
| Force Applying Frequency | 2 | 1 |
| Force Applying Occasion | Flicking action is applied after completing every suction of smoking after the second suction of smoking is taken | |
| Holding Width (mm) | 10 | |
| Hammer Width (mm) | 10 | |
| Ending Occasion (mm) | 40 ± 0.5 | 42 ± 0.5 |
| Smoking Mode | ISO3308 Standard Smoking Mode | |

Figure 1:
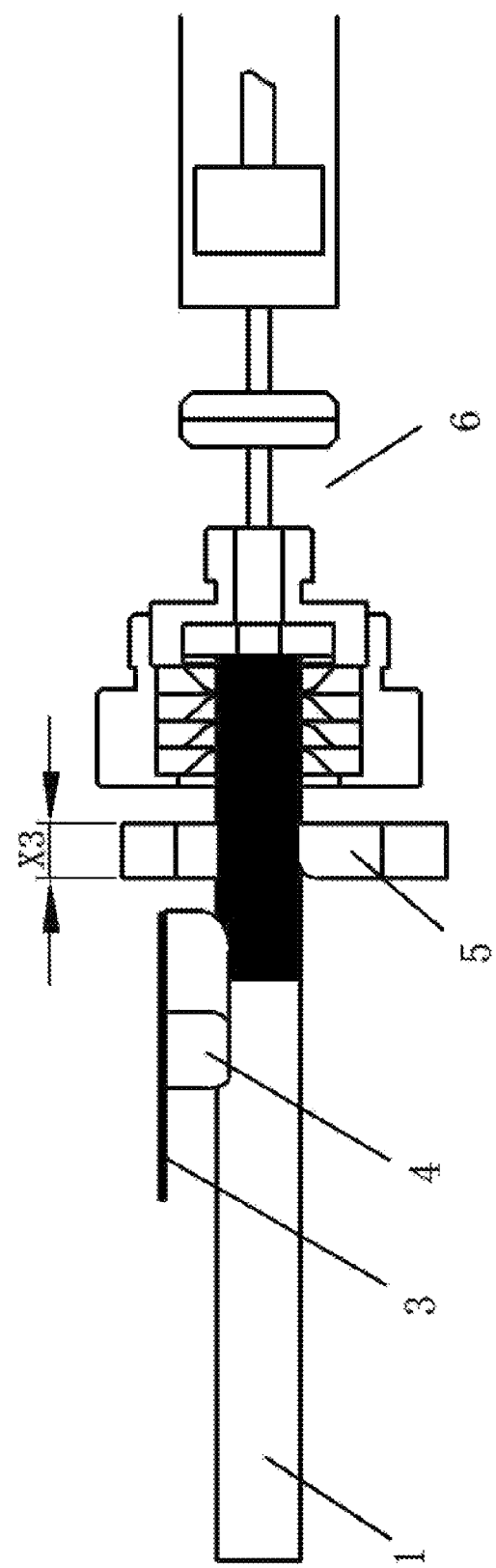
FIG. 1 is a side view of an apparatus for assessing hot coal fallout propensity of burning cigarettes based on human behavior features of ash-flicking action according to an exemplary embodiment of the present disclosure.
Figure 2:
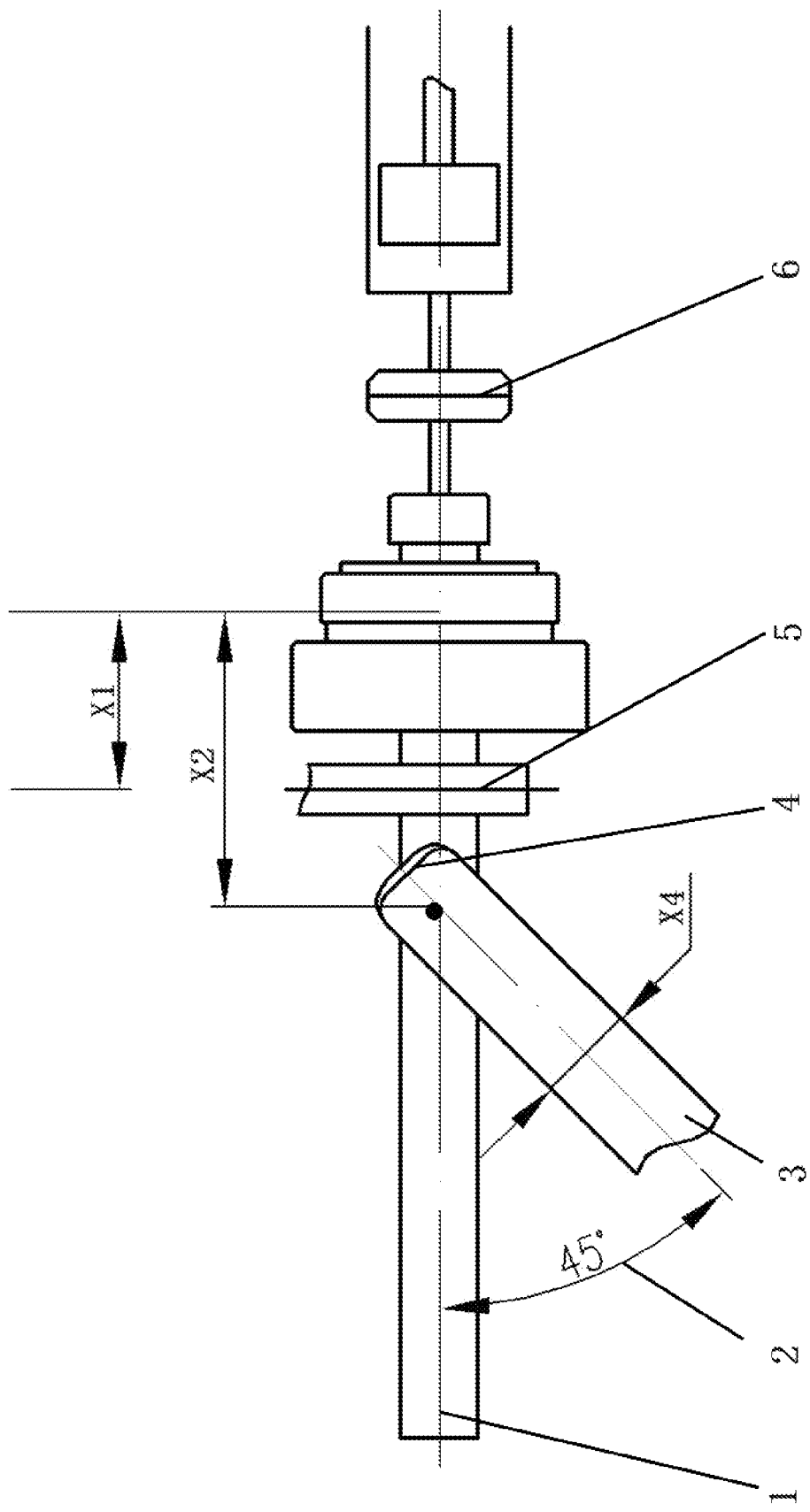
FIG. 2 is a top view of the apparatus for assessing hot coal fallout propensity of burning cigarettes based on human behavior features of ash-flicking action shown in FIG. 1.

The present disclosure may provide a testing device for hot coal fallout propensity (see FIGS. 1 and 2) in accordance with the above operating conditions. The testing device may comprise a cigarette suction unit, a holding unit and a flicking unit. The specific conditions may be described as follows:

1. With a cigarette suction unit in accordance with GB/T 16450;

2. The flicking unit may require that a Mohs hardness of a material of a flicking hammer 4 is in a range of 1-3; the width X4 of the flicking hammer 4 may conform to (10±0.5) mm; the flicking angle 2 (the angle formed between a flicking arm 3 and a cigarette 1 when cigarette ash is flicked) may be adjusted from 30° to −60°; the flicking strength (the strength of the flicking hammer 4 applied on the cigarette 1) may be adjustable within a range of (20-60) gf (tolerance±2 gf is allowed); a flicking time (the duration of flicking action applied on the cigarette 1 by the flicking hammer 4) may be maintained for 0.03 s (tolerance±0.005 s is allowed); the flicking position X2 (a distance X2 from a force applying center point of flicking action applied on the cigarette 1 by the flicking hammer 4 to a distal end of cigarette butt) is adjustable within a range of (30-32) mm (tolerance±0.5 mm is allowed); and the flicking frequency (number of times of flicking cigarette ash in one round by applying a force on the cigarette 1 by the flicking hammer 4, that is, the number of continuous force applying times per round of flicking action) may control the setting of one flicking action and 2-4 times of continuous flicking actions per round (interval time between two flicking actions may be no more than 1 s);

3. The material of a cigarette holder in the holding unit may be selected based on simulated human fingers, and its Shore hardness may be 2.7±2.3 HA; a width of the cigarette holder may be 10±0.5 mm according to smoker's flicking habit; the holding strength may be adjustable within a range of 16-18 gf and the tolerance of ±2 gf may be allowed; the holding position may be adjustable within a range of 1-20 mm and the tolerance of ±0.5 mm may be allowed; and the device may also have a control unit for controlling the flicking strength, the time of flicking action, the flicking position, the flicking occasion, the holding strength, and the holding position and similar parameter.

Embodiment 1

A King Size cigarette (brand A) may be selected as a test sample. The present disclosure may be implemented in accordance with the following test condition settings and operational steps:

A sample may be placed under a constant temperature and humidity environment and adjusted according to GB/T 16447. The laboratory test atmosphere for hot coal fallout propensity test shall also be complied with provisions of GB/T 16447.

Step 2: Setting test operational conditions according to specifications of cigarettes.

The flicking strength and the flicking action time of the detecting device for hot coal fallout propensity may be set to be 38±2 gf; the flicking position of the detecting device for hot coal fallout propensity may be set to be 30±0.5 mm; a termination mark position of hot coal fallout propensity test of burning cigarettes of the test device for hot coal fallout propensity may be set to be 40±0.5 mm; the flicking occasion of the test device for hot coal fallout propensity may be set as follows: starting from the second suction of smoking, one round of flicking is applied respectively after every suction, until the termination mark position is reached; the flicking frequency of the test device for hot coal fallout propensity may be set as follows: two flicking actions are applied per round, the interval time between two flicking actions is not more than 1 s; the holding strength of the test device for hot coal fallout propensity may be set to be 18±2 gf; the holding position of the test device for hot coal fallout propensity may be set to be 18±0.5 mm; and the smoking mode of the test device for hot coal fallout propensity may be set to be ISO3308 standard smoking mode.

Step 3: An adjusted cigarette sample is inserted into a cigarette holder and performs smoking and flicking actions under test conditions.

Step 4: When hot coal fallout occurred during smoking or the termination mark position of the cigarette hot coal fallout propensity test is reached, the test is completed and state information of "falling" and "not falling" of the cigarette hot coal and suction numbers of the fallout are recorded.

Step 5: 40 cigarettes are repeatedly tested and the cigarette hot coal fallout propensity is calculated as the result of a set of cigarettes.

Step 6: Every sample is tested for twice.

Step 7: The test results are calculated.

The results of recording test data, which present the cigarettes' hot coal fallout propensity (HCFP), are calculated according to equation (1):

$$HCFP = \frac{n}{40} \times 100\% \quad (1)$$

wherein:

HCFP—Cigarette hot coal fallout propensity, %;

n—Numbers of cigarettes having fallout phenomenon.

The numbers of cigarettes having fallout phenomenon in two sets of 40 cigarettes are 9 and 10, respectively.

Step 8: Analyzing and determining results. Two testing results are 22.5% and 25.0%, respectively. The absolute difference of the parallel test results is not more than 20.0%, and the test result is 23.8%.

Embodiment 2

A Superslim cigarette (brand B) is selected as a test sample. The present disclosure may be implemented in accordance with the following test condition settings and operational steps:

A sample may be placed under a constant temperature and humidity environment and adjusted according to GB/T16447. The laboratory test atmosphere for hot coal fallout propensity test shall also be complied with provisions of GB/T16447.

Step 2: Setting test operational conditions according to specifications of cigarettes.

The flicking strength and the flicking action time of the detecting device for hot coal fallout propensity performance may be set to be 32±2 gf; the flicking position of the detecting device for hot coal fallout propensity performance may be set to be 32±0.5 mm; a termination mark position of hot coal fallout propensity test of burning cigarettes of the test device for hot coal fallout propensity may be set to be 42±0.5 mm; the flicking occasion of the test device for hot coal fallout propensity may be set as follows: starting from the second suction of smoking, one round of flicking is applied respectively after every suction, until the termination mark position is reached; the flicking frequency of the test device for hot coal fallout propensity may be set as follows: one flicking action is applied per round; the holding strength of the test device for hot coal fallout propensity may be set to be 16±2 gf; the holding position of the test device for hot coal fallout propensity may be set to be 19±0.5 mm; and the smoking mode of the test device for hot coal fallout propensity may be set to be ISO3308 standard smoking mode.

Step 3: An adjusted cigarette sample is inserted into a cigarette holder and performs smoking and flicking actions under test conditions.

Step 4: When hot coal fallout occurred on the cigarette butt during smoking or the termination mark position of the cigarette hot coal fallout propensity test is reached, the test is completed and state information of "falling" and "not falling" of the cigarette hot coal and suction numbers of the fallout are recorded.

Step 5: 40 cigarettes are repeatedly tested and the cigarette hot coal fallout propensity is calculated as the result of a set of cigarettes.

Step 6: Every sample is tested for twice.

Step 7: The test results are calculated.

The results of recording test data, which present the cigarette hot coal fallout propensity (HCFP), are calculated according to equation (1):

$$HCFP = \frac{n}{40} \times 100\% \tag{1}$$

wherein:

HCFP—Cigarette hot coal fallout propensity, %;

n—Numbers of cigarettes having fallout phenomenon.

The numbers of cigarettes having fallout phenomenon in two sets of 40 cigarettes are 6 and 6, respectively.

Step 8: Analyzing and determining results. Two testing results are 15.0% and 15.0%, respectively. The absolute difference of the parallel test results is not more than 20.0%, and the test result is 15.0%.

What is claimed is:

1. An apparatus for assessing hot coal fallout propensity of burning cigarettes based on human behavior features of ash-flicking action, comprising:
   a holding unit for holding a cigarette;
   a suction unit connected to one end of the cigarette to suck the cigarette;
   a flicking unit disposed adjacent to the holding unit, and the flicking unit being capable of flicking the cigarette; and
   a control unit coupled with the suction unit and the flicking unit, respectively, to control suction and flicking actions,
   wherein the flicking unit comprises:
   a flicking arm; and
   a flicking hammer disposed at one end of the flicking arm to flick the cigarette under driving of the flicking arm, and an angle between the flicking arm and the cigarette being between 30°-60° when the flicking hammer is in contact with the cigarette.

2. The apparatus according to claim 1, wherein the holding unit is disposed at a filter tip of the cigarette, and the one end of the cigarette is a free end of the filter tip.

3. The apparatus according to claim 1, wherein the flicking hammer is made of a material with a Mohs hardness in a range of 1-3.

4. The apparatus according to claim 1, wherein a flicking strength of the flicking hammer applied on the cigarette is between 20 gf-60 gf.

5. The apparatus according to claim 1, wherein duration for every flicking action applied by the flicking hammer is between 0.025 seconds-0.035 seconds.

6. The apparatus according to claim 1, wherein a width of a flicking point, where the flicking hammer flicks at the cigarette, is between 9.5 mm-10.5 mm, and a distance between the flicking point and the one end of the cigarette is between 30 mm-32 mm.

7. The apparatus according to claim 1, wherein the holding unit is made of a material with a Shore hardness in a range of 0.4 HA-5.0 HA.

8. The apparatus according to claim 1, wherein a holding width of the holding unit holding the cigarette is between 9.5 mm-10.5 mm, a holding strength of the holding unit is between 16 gf-18 gf, and a distance from a holding point of the holding unit to the one end of the cigarette is between 18 mm-20 mm.

9. The apparatus according to claim 1, wherein the control unit is used to control a holding strength of the holding unit, a suction strength and a suction frequency of the suction unit, and a flicking cycle, a position of a flicking point and a flicking strength of the flicking unit.

10. A method for assessing hot coal fallout propensity of burning cigarettes by using the apparatus for assessing hot coal fallout propensity of burning cigarettes according to claim 1, comprising:
   step A: using the holding unit to hold the cigarette and ignite the cigarette;
   step B: activating the suction unit by the control unit to suck the cigarette, so as to simulate smoking action of human;
   step C: taking k times suction by the suction unit as a cycle, and activating the flicking unit by the control unit to perform a round of flicking actions on the cigarette to simulate human's flicking actions;

step D: stopping detection by the control unit when the cigarette has fallout or the cigarette is burned to a predetermined test termination mark; and step E: repeating the step B, the step C and the step D for 40 cigarettes, and recording an occurrence number n of fallout so as to calculate hot coal fallout propensity (HCFP) of burning cigarettes by using the following formula:

HCFP=$n$/40×100%.

11. The method according to claim 10, wherein the step A, the step B, the step C, the step D, and the step E are performed in a constant temperature and humidity environment.

12. The method according to claim 10, wherein a holding width of the holding unit holding the cigarette is between 9.5 mm-10.5 mm, and a holding strength of the holding unit is between 16 gf-18 gf, and a distance from a holding point of the holding unit to the one end of the cigarette is between 18 mm-20 mm.

13. The method according to claim 10, wherein in the step C, the round of flicking actions comprise performing 1-4 times of flicking actions on the cigarette by using the flicking unit, and an interval time between adjacent two flicking actions is no longer than 1 second.

14. The method according to claim 10, wherein in the step C, a flicking strength of the flicking hammer applied on the cigarette is between 20 gf-60 gf.

15. The method according to claim 10, wherein in the step C, a width of a flicking point, where the flicking hammer flicks at the cigarette, is between 9.5 mm-10.5 mm, and a distance between the flicking point and the one end of the cigarette is between 30 mm-32 mm.

16. The apparatus according to claim 10, wherein two sets of tests are applied to each cigarette sample, a final HCFP of the cigarette is represented by an average value of the two sets of detection results after the step E, and the detection is performed again when an absolute difference of two sets of detection results is greater than 20%.

* * * * *